US006843654B1

(12) United States Patent
Liu

(10) Patent No.: US 6,843,654 B1
(45) Date of Patent: Jan. 18, 2005

(54) DENTAL PROSTHESIS

(75) Inventor: Andrew T. C. Liu, York, PA (US)

(73) Assignee: Dentsply Research & Development Corp.

( * ) Notice: Subject to any disclaimer, the term of this patent is extended or adjusted under 35 U.S.C. 154(b) by 0 days.

(21) Appl. No.: 09/567,702

(22) Filed: May 10, 2000

Related U.S. Application Data

(63) Continuation of application No. 09/333,727, filed on Jun. 15, 1999, now Pat. No. 6,139,322, which is a continuation of application No. 08/447,296, filed on May 22, 1995, now abandoned, which is a division of application No. 07/979,093, filed on Nov. 19, 1992, now abandoned, which is a continuation-in-part of application No. 07/729,018, filed on Jul. 12, 1991, now abandoned.

(30) Foreign Application Priority Data

| Jun. 23, 1992 | (AU) | ............................................. 18520/92 |
| Jun. 24, 1992 | (CA) | ............................................. 2072205 |
| Jul. 10, 1992 | (EP) | ............................................. 92111787 |
| Jul. 12, 1992 | (JP) | ............................................. 4/185532 |

(51) Int. Cl.$^7$ ......................................... A61C 13/087
(52) U.S. Cl. .................................. 433/202.1; 523/115
(58) Field of Search ....................... 433/202.1; 523/113, 523/115, 116, 118, 120; 525/55, 192, 191; 526/242; 623/16.11, 16

(56) References Cited

U.S. PATENT DOCUMENTS

| 2,315,503 | A | 4/1943 | Crowell et al. ............... 250/36 |
| 2,345,305 | A | 3/1944 | Thornton .................... 18/55.1 |
| 2,403,172 | A | 7/1946 | Crowell et al. ............... 250/36 |
| 2,532,502 | A | 12/1950 | Van Beuren Joy ......... 250/45.5 |
| 2,673,194 | A | 3/1954 | Grim ........................ 260/93.5 |
| 3,066,112 | A | 11/1962 | Bowen ........................ 260/41 |
| 3,084,436 | A | 4/1963 | Landry ........................... 32/2 |
| 3,087,875 | A | 4/1963 | Graham ..................... 204/154 |
| 3,338,985 | A | 8/1967 | Magat et al. ............... 260/830 |
| 3,427,274 | A | 2/1969 | Cornell ..................... 260/31.8 |
| 3,452,437 | A | 7/1969 | Chang .......................... 32/15 |
| 3,468,977 | A | 9/1969 | Bruckmann et al. ........ 260/885 |
| 3,469,317 | A | 9/1969 | Jarby ........................... 32/15 |
| 3,470,615 | A | 10/1969 | Petner .......................... 32/12 |
| 3,471,596 | A | 10/1969 | Petner et al. ................. 264/19 |
| 3,488,846 | A | 1/1970 | Cornell ........................... 32/8 |
| 3,508,128 | A | 4/1970 | Allison ...................... 317/258 |
| 3,539,533 | A | 11/1970 | Lee, II et al. ................. 260/47 |
| 3,597,389 | A | 8/1971 | Taylor ......................... 260/41 |
| 3,629,187 | A | 12/1971 | Waller ........................ 260/41 |
| 3,647,498 | A | 3/1972 | Dougherty .................... 117/8 |
| 3,649,608 | A | 3/1972 | Logemann et al. ......... 260/885 |
| 3,751,399 | A | 8/1973 | Lee, Jr. et al. ............... 260/17 |
| 3,833,404 | A | 9/1974 | Sperling et al. ............. 117/63 |
| 3,923,740 | A | 12/1975 | Schmitt et al. ............... 260/47 |

(List continued on next page.)

FOREIGN PATENT DOCUMENTS

| AU | 50674/78 | 7/1974 |
| CA | 1069239 | 1/1980 |
| CA | 1173991 | 9/1984 |
| CA | 1236617 | 10/1988 |
| CA | 1269470 | 5/1990 |
| CA | 2023942 | 8/1990 |
| CA | 2029032 | 10/1990 |
| DE | 258641 | 7/1986 |
| EP | 329176 | 8/1989 |
| EP | 358195 | 3/1990 |
| EP | 529264 | 3/1993 |
| WO | 82/02556 | 8/1982 |
| WO | 91/16013 | 10/1991 |

OTHER PUBLICATIONS

STN/CAS online, file PROMT, Acc. No. 89:68854 (Chemical Week (Apr. 5, 1989), p. 17), Abstract.*
SAE/Design Engineering Meetings—Air products develop additive for cast PU; Mar. 21, 1988.
Air Products—PRIMAX—Air Products and Chemicals, Inc. 1989.
High Abrasive Resistance, 1983, American Hoechst Corporation.
"An evaluation of triad VLC acrylic for general use in orthodontics", by V.S.J. Jones, pp. 20–22, "The Dental Technician", 1950.
Observations on the Elastic Behavior of an Synthetic Orthodontic Elastomer by E.F. Huget, K.S. Patrick and L.J. Nunez pp. 496–501 *J. Dent Res,* Feb. 1990.
"Effect of Monomer Structure on the Mechanical Properties of Light–cured Unfilled Resins" by Kawaguchi, fukushima and Horibe, pp. 174–181 *Dental Materials Journal*7(2): (1988).
"Surface free energy and deposit adhesion studied" *Dental Abstracts* Jan.–Feb. 1990.
CA Selects: *Croslinking reactions* Issue 15, 1990 pp. 10, 14–16 particularly p. 10; Paragraph 113:7822e; p. 14–5 paragraph 113:12075t; p. 16 paragraph 112:240451x.
"Studies on Adhesive Monomers for Teeth V. Influence of Substituents in Methacrylamide Derivatives" by Kitoh and Miyake, *Journal of Applied Polymer Science,* vol. 39, 103–108 (1990).

(List continued on next page.)

*Primary Examiner*—S. Mark Clardy
*Assistant Examiner*—Frank Choi
(74) *Attorney, Agent, or Firm*—Douglas J. Hura; James B. Bieber

(57) ABSTRACT

A dental composition comprising self-lubricating particles and formed into a dental tooth. The invention provides a dental tooth formed from a composition which includes polymeric matrix material and particles of ultrahigh molecular weight polyethylene having a particle size less than 500 microns, and a weight average molecular weight greater than 1,000,000 g/mole chemically bonded to the matrix material and the composition formed into an aesthetic dental tooth. The tooth has an outer face, and at least one of the particles is smeared over the outer face.

10 Claims, 1 Drawing Sheet

U.S. PATENT DOCUMENTS

| | | | |
|---|---|---|---|
| 3,928,299 A | 12/1975 | Rosenkranz et al. ........ | 260/89.5 |
| 3,961,379 A | 6/1976 | Highgate ......................... | 3/13 |
| 4,020,557 A | 5/1977 | Rockett et al. ................. | 32/15 |
| 4,197,234 A | 4/1980 | Temin ..................... | 260/42.27 |
| 4,199,864 A | 4/1980 | Ashman ..................... | 433/175 |
| 4,244,689 A | 1/1981 | Ashman ..................... | 433/175 |
| 4,267,097 A | 5/1981 | Michl et al. ............. | 260/42.15 |
| 4,281,991 A | 8/1981 | Michl et al. ................. | 433/202 |
| 4,288,221 A | 9/1981 | Engel ......................... | 433/202 |
| 4,300,886 A | 11/1981 | Suling et al. ............... | 433/202 |
| 4,302,376 A | 11/1981 | Walkowiak et al. .......... | 106/35 |
| 4,308,190 A | 12/1981 | Walkowiak et al. ........ | 260/29.7 |
| 4,361,676 A | 11/1982 | Simpson ..................... | 525/118 |
| 4,369,262 A | 1/1983 | Walkowiak et al. ........ | 523/109 |
| 4,396,377 A | 8/1983 | Roemer ...................... | 433/199 |
| 4,396,476 A | 8/1983 | Roemer et al. ........ | 204/159.16 |
| 4,398,007 A | 8/1983 | Kubota ......................... | 526/273 |
| 4,439,380 A | 3/1984 | Michl et al. .................... | 264/16 |
| 4,547,390 A | 10/1985 | Ashman et al. ................. | 427/2 |
| 4,552,906 A | 11/1985 | Podszun et al. ............. | 523/115 |
| 4,598,111 A * | 7/1986 | Wright et al. | |
| 4,650,418 A | 3/1987 | Blair et al. .............. | 433/203.1 |
| 4,698,373 A * | 10/1987 | Tateosian et al. | |
| 4,719,149 A | 1/1988 | Aasen et al. ................. | 428/473 |
| 4,761,436 A | 8/1988 | Kohno et al. ................. | 522/114 |
| 4,771,110 A | 9/1988 | Bauman et al. ............. | 525/131 |
| 4,787,850 A | 11/1988 | Michl et al. ................. | 433/224 |
| 4,813,876 A | 3/1989 | Wang ......................... | 433/224 |
| 4,814,362 A | 3/1989 | Billington et al. .......... | 523/117 |
| 4,814,423 A | 3/1989 | Huang et al. ................. | 528/230 |
| 4,816,495 A | 3/1989 | Blackwell et al. ............. | 522/14 |
| 4,826,893 A | 5/1989 | Yamazaki et al. .......... | 523/115 |
| 4,829,127 A | 5/1989 | Muramoto et al. ......... | 525/309 |
| 4,832,745 A | 5/1989 | Antonucci .................... | 106/35 |
| 4,843,136 A | 6/1989 | Reiners et al. .............. | 526/279 |
| 4,863,977 A | 9/1989 | Tateosian et al. ............. | 522/14 |
| 4,868,325 A | 9/1989 | Reiners et al. .............. | 560/115 |
| 4,872,936 A | 10/1989 | Engelbrecht ............. | 156/307.3 |
| 4,877,401 A | 10/1989 | Higuchi et al. ............. | 433/215 |
| 4,879,402 A | 11/1989 | Reiners et al. ................ | 560/26 |
| 4,880,879 A * | 11/1989 | Bauman | |
| 4,882,365 A | 11/1989 | Gasser et al. ................ | 523/117 |
| 4,884,866 A | 12/1989 | Hashimoto et al. ...... | 350/96.34 |
| 4,891,400 A | 1/1990 | Schwabe et al. ............ | 524/745 |
| 4,894,012 A | 1/1990 | Goldberg et al. ........... | 433/215 |
| 4,894,315 A | 1/1990 | Feinberg et al. ............. | 430/281 |
| 4,902,228 A | 2/1990 | Reiners et al. ........... | 433/228.1 |
| 4,904,750 A | 2/1990 | Reiners et al. .............. | 526/301 |
| 4,909,738 A * | 3/1990 | Ai et al. | |
| 4,937,144 A | 6/1990 | Podszun et al. ............ | 428/402 |
| 4,956,252 A | 9/1990 | Fryd et al. .................. | 430/133 |
| 4,970,037 A | 11/1990 | Kafka et al. ................ | 264/101 |
| 6,384,107 B2 * | 5/2002 | Liu ............................ | 523/118 |

OTHER PUBLICATIONS

UHMWPE: When The Going Gets Tough—Materials Engineering, Jan. 1992; pp. 23 and 24. Stevens.

NERAC Self Lube RPA—346 Apr. 8, 1992—Question No. 769463 Tech. Spec. John Russell.

NERAC Self Lube NPA—34 Apr. 8, 1992 Question No. 769463 Tech. Spec. John Russell.

NERAC Self Lube PMT—345 Apr. 8, 1992 Question No. 769463 Tech. Spec. John Russell.

* cited by examiner

DENTAL PROSTHESIS

This application is a continuation of patent application Ser. No. 09/333,727 filed Jun. 15, 1999, now U.S. Pat. No. 6,139,322, which is a continuation of patent application Ser. No. 08/447,296, filed May 22, 1995; now abandoned, which is a division of patent application Ser. No. 07/979,093 filed Nov. 19, 1992 now abandoned, which is a continuation-in-part of patent application Ser. No. 07/729,018 filed Jul. 12, 1991 now abandoned.

BACKGROUND OF THE INVENTION

The invention relates to self-lubricating abrasion resistant compositions useful for a wide range of applications. Particular utility is found in the dental and medical arts where such compositions are suitable for the formation and construction of dental prosthesis such as artificial teeth, inlays, onlays, and facings, crowns and bridges and artificial bone parts and medical prosthetic body parts, such as knee joints and/or other bone engaged surfaces and the like where abrasion resistance, polishability and: aesthetics are important.

Artificial teeth should exhibit certain physical and physiochemical characteristics to be suitable for use. They should be hard and resistant to chipping, durable, and stable to solvents, water, and heat. In addition, they should be of an aesthetically acceptable color, i.e., close to that of natural teeth, or be amenable to artificial coloration. The teeth should not cause excessive wear to opposing natural or artificial teeth, should not wear out of occlusion, and should be capable of being bonded firmly to supportive structures. They should also be amenable to ordinary means of physical shaping, grinding, and polishing, so as to minimize production costs.

Various metals and ceramics as used in the formation of prior art artificial teeth and other dental appliances possess certain inherent deficiencies which lessen their desirability in dental applications. Thus, the metallic color of gold, amalgam, and other metallic species serves as an aesthetic detraction to the wearer of appliances made therefrom. In addition, the high cost of most noble metals from which many such appliances are commonly made leads to a cost consideration whenever their use is contemplated. Ceramic materials, another common alternative, are often difficult to form into acceptable shapes, and may tend to be abrasive and aesthetically unpleasant subsurfaces upon the physical wearing of surface layers. Such materials are also difficult to polish satisfactorily. These reasons together with factors related to cost, to consumer preference, to the technical skills of dental practitioners, and to convenience have motivated a search for alternative compositions suitable for the construction of dental appliances, inlays, onlays, crown and bridge material, artificial teeth and the like.

Of the presently available organic compositions used for the construction of artificial teeth, most are composed of acrylics, often crosslinked by polyfunctional moieties.

As used herein "self-lubricating material" means a material which is adapted to increase the lubricity of a product surface. Preferably self-lubricating material for use as particles in prostheses in accordance with the invention has a kinetic coefficient of friction less than 0.25 when measured using ASTM D 1894-78 with a load of 5 psi.

As used herein ASTM D 1894-78 is carried out using water and the same materials.

As used herein "water insensitive" means that water does not have a material effect upon the material so characterized.

It is to be understood that the term "bisphenol-A" is commonly utilized in the art to indicate the chemical compound 2,2-bis(4-hydroxyphenyl)propane. It is also to be understood that the term "bis-GMA" is commonly used to indicate the chemical compound 2,2-bis(4-(2-hydroxy-3-methacryloxypropoxy)phenyl)propane, otherwise referred to as "digycidyl methacrylate ester of bisphenol-A."

Dentsply U.S. Pat. Nos. 4,396,476, 4,396,377 and 4,698,373 (the disclosures of which are incorporated herein by reference) disclose interpenetrating network teeth but do not disclose self-lubricating abrasion resistant compositions as required by the applicant's invention.

Thornton U.S. Pat. No. 2,345,305 discloses making artificial teeth comprised of different plastic materials for the face ("enamel") and body portions. Note FIG. 17, and page 4, column 2, lines 21–24. Another composite plastic tooth structure is disclosed by Cornell U.S. Pat. No. 3,488,846.

The Rosenkranz et al. U.S. Pat. No. 3,928,299 discloses an organic homopolymer or random copolymer containing urethane groups.

Michl et al. in U.S. Pat. Nos. 4,267,097 and 4,281,991 (the disclosures of which are incorporated herein by reference) disclose artificial teeth prepared from (a) particle/bead PMMA, (b) a liquid monomer such as the adduct of hydroxymethacrylates and diisocyanates or difunctional esters of (meth)acrylic acids or mixtures thereof, and (c) micro-fine inorganic fillers. Michl et al do not disclose self-lubricating abrasion resistant hardenable compositions as required by Applicants' invention.

Walkowiak et al. in U.S. Pat. Nos. 4,308,190 and 4,369,262 disclose dental paste materials of a polymerizable acrylic ester, a crosslinked bead polymer, and a particulate inorganic filler and do not disclose self-lubricating abrasion resistant hardenable compositions, or interpenetrating network compositions for making artificial teeth as required by Applicants' invention.

Simpson in U.S. Pat. No. 4,361,676 discloses a sag-resistant, pumpable composition comprising a liquid material dispersed throughout a synthetic, continuous crosslinked polymer matrix.

Wright et al. in U.S. Pat. No. 4,598,111 disclose the use of various divinyl compounds, including divinyl dimethylsilane (column 6, line 35) as a crosslinking agent for (meth)-acrylate monomer systems. Other patents of this general type include, for example, Kohno et al. U.S. Pat. No. 4,761,436; dimethyldivinylsilane as a co-monomer; column 3, line 29); Feinberg et al. U.S. Pat. No. 4,894,315; column 3, lines 37–38); Fryd et al. U.S. Pat. No. 4,956,252; column 5, lines 43–44); and Kafka et al. U.S. Pat. No. 4,970,037; column 9, lines 16–17).

Yamazaki et al. in U.S. Pat. No. 4,826,893 disclose a dental composition comprising (a) a siloxane polymer, (b) a monomer copolymerizable with the siloxane polymer, (c) a polymerization catalyst, e.g. benzoyl peroxide, and optionally, (d) a filler.

Laundry in U.S. Pat. No. 3,084,436 discloses soft dental materials manufactured from mixtures of methacrylate monomers. Monofunctional esters together with vinyl-acetate or vinyl stearate are crosslinked with polyfunctional esters of acrylic or met acrylic acid. The resulting product is disclosed as being three dimensionally crosslinked.

Graham et al. in U.S. Pat. No. 3,087,875 disclose preparation of graft copolymers. Alkyl methacrylate and analogous polymers are dissolved in monomers such as alkyl acrylates, alkyl thioacrylates, and N-vinyl lactams. The monomers are subsequently grafted to the preformed polymers via photochemical initiation.

Cornell in U.S. Pat. No. 3,427,274 discloses hard-enable materials formed from a mixture of methyl methacrylate homopolymer and styrene-butadiene copolymer latex coated with methyl methacrylate polymer which may be incorporated in a methacrylate-crosslinking agent composition to form hardenable compositions.

Chang in U.S. Pat. No. 3,452,437 discloses a dental restorative material formed from the "diglycidyl methacrylate of bisphenol-A" (bis-GMA) to which a quantity of methyl methacrylate may be added.

Bruckmann et al. in U.S. Pat. No. 3,468,977 disclose the formulation of dental compositions from a mixture of a polymer and a monomer. The preformed uncrosslinked polymer beads are allowed to swell with monomer which may contain a crosslinking agent. Acrylic materials may be used for both the monomer and the polymer. Petner in U.S. Pat. No. 3,470,615, teaches the formulation of a material suitable for use in the construction of dental appliances. A mixture of an uncrosslinked homopolymer and crosslinked copolymer is dissolved in a liquid polyglycol dimethacrylate to form a suspension which may be brushed on a substratum and subsequently hardened by heat to build up layers of polymeric material. A similar teaching may be found in U.S. Pat. No. 3,471,596, also to Petner et al. A thick liquid is provided which is useful in the building up of dental crowns and the like. The difunctional monomer may contain various thickening agents including poly(methyl methacrylate). In some embodiments, the poly (methyl methacrylate) may be supplemented with additional polymer which may be partially crosslinked with allyl methacrylate.

Lee in U.S. Pat. No. 3,539,533 discloses a filling material including a monomer solution filled with inorganic particulate filler. The monomer solution may be a mixture of methacrylate monomers containing bisphenol-A dimethacrylate.

Taylor in U.S. Pat. No. 3,597,389 discloses polyfunctional methacrylate monomers, including "bis-phenol-A glycidyl dimethacrylate" (bis), polymerized with an inorganic filler to yield dental compositions.

Waller in U.S. Pat. No. 3,629,187 discloses the use of the isocyanate or diisocyanate adducts of bisphenol-A type compounds. These adducts are employed together with various inorganic fillers and liquid monomers to form liquid or paste compositions which are polymerizable either thermally or photochemically.

Dougherty in U.S. Pat. No. 3,647,498 discloses dental compositions which are composed of liquid-solid mixtures. The solid phase is an acrylate or methacrylate polymer in bead form.

Logemann in U.S. Pat. No. 3,649,608 discloses dental compositions which comprise solid bead polymers or copolymers of methacrylate type materials.

Lee in U.S. Pat. No. 3,751,399 discloses compositions for dental use comprising aromatic and alicyclic polyacrylates which are mixed together with other polyacrylate compounds especially those containing bisphenol-A structures.

Sperling in U.S. Pat. No. 3,833,404 discloses elastomers, especially acrylates, urethanes, butadienes, natural rubbers, and polyvinyl alcohol, are formulated which possess interpenetrating polymeric network type structures. These materials are disclosed as being "hard", but are used as vibration and sound damping insulators.

Highgate in U.S. Pat. No. 3,961,379 discloses an article manufactured from a crosslinked polymer which is swollen with a monomer containing a crosslinking agent.

Temin in U.S. Pat. No. 4,197,234 discloses dental restorative composite compositions and filler therefor.

Engel in U.S. Pat. No. 4,288,221 discloses durable polishable direct filling material.

Jarby in U.S. Pat. No. 3,469,317 discloses material for filling cavities.

Crowell in U.S. Pat. No. 2,315,503 discloses art of molding composite resins.

Crowell in U.S. Pat. No. 2,403,172 discloses art of molding resins of vinyl type.

Van Beuren Joy in U.S. Pat. No. 3,532,502 discloses dentures, compositions, and methods.

Michl et al in U.S. Pat. No. 4,281,991 discloses dental prostheses.

Bauman et al in U.S. Pat. No. 4,771,110 discloses polymeric materials having controlled physical properties and processes for obtaining these.

Muramoto et al in U.S. Pat. No. 4,829,127 discloses composite resin particles, its preparation and resinous composition for coating use containing the same.

Bauman in U.S. Pat. No. 4,880,879 discloses abrasion resistant composite material and process for making the same.

Podszun et al in U.S. Pat. No. 4,937,144 discloses dental fillers.

Lee in Australian Patent Specification 50,674 discloses dental adhesive composites.

None of the foregoing patents discloses the novel compositions and prostheses having matrix material bonded or adapted to be banded to self-lubricating abrasion resistant particles in accordance with the invention.

OBJECTS OF THE INVENTION

It is an object of the invention to provide abrasion resistant dental compositions especially useful as dental appliances, dentures and other prosthesis, inlays, onlays, facings, crowns and bridges and the like.

It is an object of the invention to provide a tooth which includes self-lubricating polymer.

It is an object of the invention to provide a dental composition including a polymeric matrix material and self-lubricating particles.

It is an object of the invention to provide a composition for dental uses, such as the formation of prosthetic devices, including self-lubricating material, a monomeric matrix forming material and inorganic filler.

It is an object of the invention to provide a dental composition including self-lubricating particles.

It is an object of the invention to provide a dental composition having self-lubricating abrasion resistant particles which are supported by and chemically bonded to a polymeric matrix material.

It is an object of the invention to provide a dental product, such as, a dental prosthesis, artificial tooth, inlay, onlay, facing, crown or bridge which is wear resistant and self-lubricating across its entire cross section.

It is an object of the invention to provide an artificial tooth including polyethylene particles having a molecular weight of at least 500,000, and a particle size less than 80 microns and are supported by and bonded to in an interpenetrating network polymer composition.

It is an object of the invention to provide compositions which are useful in the construction of artificial teeth and other dental appliances, which compositions lead to products having superior physical and aesthetic characteristics.

BRIEF SUMMARY OF THE INVENTION

Dental composition and prosthesis including a self-lubricating material. The dental composition is used to form dental products having reduced wear. The dental products formed are abrasion resistant and self-lubricating across their entire cross sections. In a preferred embodiment the self-lubricating material is selected from among those having coefficients of friction one-half or less of that for polymethyl methacrylate. The particles are reacted so they may be chemically bonded to the polymer matrix within which they are dispersed. In a preferred embodiment polyethylene particles having a molecular weight of at least 1,000,000, and a particle size less than 80 microns are dispersed within an acrylate or methacrylate polymer matrix. The composition is formed into a dental prosthesis, such as an artificial tooth, inlay, onlay, facing, crown or bridge.

DETAILED DESCRIPTION OF THE INVENTION

Dental compositions of matter are described which include self-lubricating polymeric material. The dental compositions are molded to form dental prosthesis having reduced abrasive wear. While not wishing to be held to any theory describing the mechanism operative by which additions of self-lubricating polymer improves abrasion resistance, it is hypothesized that as the matrix polymer is worn away new particles of the self-lubricating abrasion resistant polymer bonded to the matrix are exposed which smear over the surface of the molded article to provide a modified surface with lower coefficient of friction and consequent improved abrasive wear resistance. Self-lubricating particles are bonded to the martix material to avoid being torn or otherwise removed in-toto from the matrix during conditions of abrasive wear. The dental produces formed show improved abrasion resistant and preferably are self-lubricating across their entire cross sections. In a preferred embodiment the self-lubricating material preferably includes polyethylene particles having a molecular weight of at least 1,000,000, and a particle size less than 80 microns. The composition is formed into a dental prosthesis, artificial tooth, inlay, onlay, facing, crown or bridge.

Figure 2:
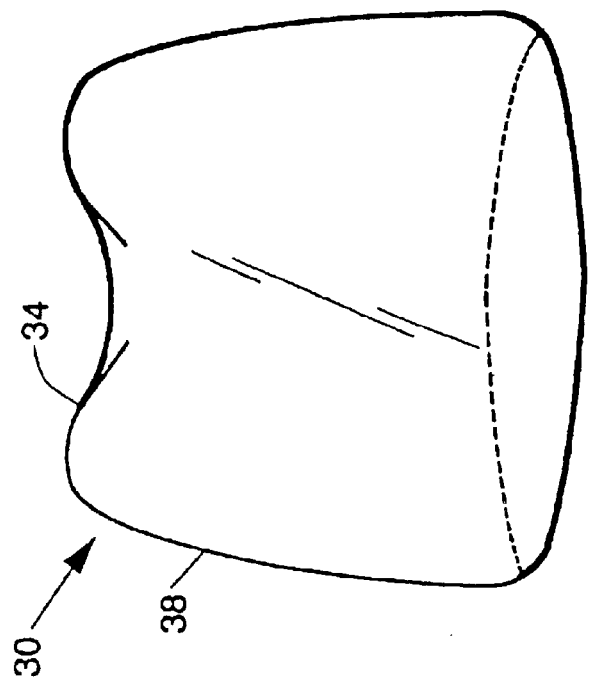
FIG. 2 is a front view of an posterior tooth in accordance with the invention.
Figure 1:
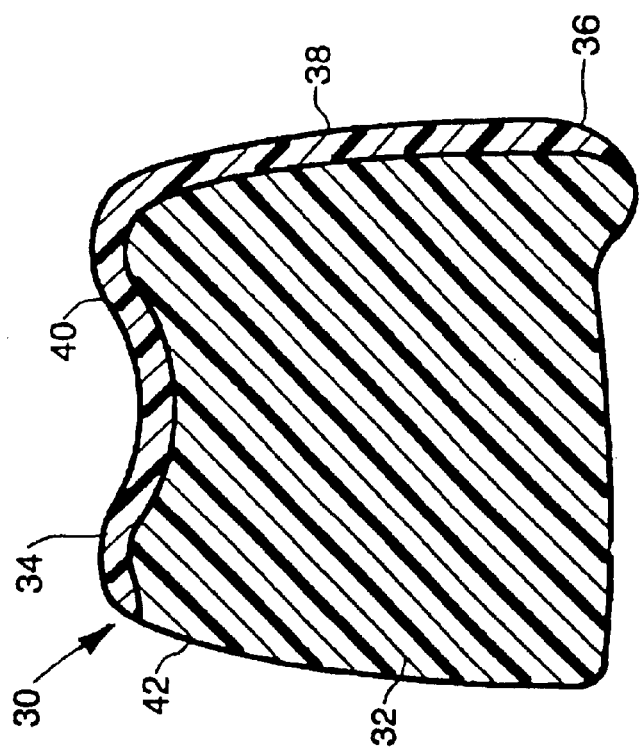
FIG. 1 is a cross-sectional side view of an posterior tooth in accordance with the invention.

The invention is now discussed with more particular reference to FIGS. 1 and 2 in which like numerals refer to the same component. FIGS. 1 and 2 show an artificial posterior tooth 30 having a tooth body 32 and an enamel coating 34. Tooth 30 includes ridge lap 36, buckle face 38, occlusal face 40 and lingual face 42. In a preferred embodiment tooth body 32 includes high molecular weight self-lubricating particles in an interpenetrating polymer network (IPN) composition. Enamel 34 includes self-lubricating abrasion resistant particles in an interpenetrating network composition.

The self-lubricating material preferably is added in the form of particles and fibers. Most preferably, these self-lubricating particles are micron-sized particles of ultra-high molecular weight polyethylene that have been functionalized by oxidation by gas plasma treatment preferably in the presence of a fluorine containing gas. Preferably particles of high molecular weight polyethylene, included as self-lubricating material in dental prosthesis in accordance with the invention, have a particle size less than 80 microns.

Self-Lubricating

Preferably the self-lubricating abrasion resistant material includes a polymers and copolymers of the general formula (I):

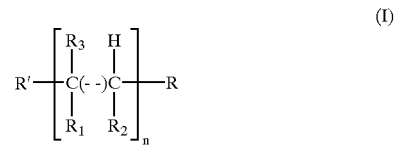

wherein n is an integer from 100 to 1,000,000,
(--) is a single or a double bond;
when (--) is a double bond R, R', and $R_3$ independently are hydrogen, or a lower alkyl of from 1 to 6 carbons, and $R_1$ and $R_2$ are not present; when (--) is a single bond R, R', $R_1$, $R_2$, and $R_3$ independently are hydrogen, fluorine or a lower alkyl of from 1 to 6 carbons.

Such polymers have a coefficient of friction of less than about one-half that of polymethyl methacrylate, or about 0.25 or less when measured using ASTM D 1894-78 with a load approximating 5 psi. An essential characteristic of the polymers and copolymers chosen is that their surface is capable of being bonded to the chosen matrix. A preferred method of achieving this is to oxidize or otherwise functionalize the particle surface as, for example, through oxyfluorination at elevated temperatures or gas plasma treatment. This requires the abstraction of hydrogen from the polymer chain. Accordingly polytetrafluoroethylene or polytetrachloroethylene are unsuitable for use according to this invention. In contradistinction polymers such as trifluoroethylene or difluoroethylene, monofluoroethylene or polyethylene or polyproppylene, for example, with molecular weights greater than 500,000 or preferably 1,000,000 or more which may be functionalized in this manner are among preferred self-lubricating materials.

In a preferred embodiment ultrahigh molecular weight polyethylene with dynamic coefficient of friction in water against steel of 0.05–0.10 was utilized as the self-lubricating material ("Ultrahigh Molecular Weight Polyethylenes" by H. L. Stein,: Engineering Plastics, Vol.2, 1988, ASM, Materials Part, Ohio). In comparision, the static coefficient of friction of polymethylmethacrylate against steel (CRC Handbook of Chemistry and Engineering, 60th edition, 1190, pages F-21, F-23) is 0.4–0.5.

Preferably self-lubricating material within the scope of general formula (I) is in the form of particles which have been treated with a fluorine containing gas as disclosed by Bauman et al in U.S. Pat. No. 4,771,110, incorporated herein by reference in its entirety to generage functional reactive sites in the surface layer of the particles. For example, particles of UHMWPE having functional reactive sites in the surface layer are sold by Air Products and Chemicals, Inc. under the trademark PRIMAX.

Dental Uses

Artificial teeth and other dental prostheses which are prepared from hardenable dental compositions in accordance with one preferred embodiment of the invention have outer face(s) which include polymeric self-lubricating material. For example, occlusal portions, i.e. "enamel", of artificial teeth are molded from compositions of the invention and are laminated over the tooth body (32 of FIG. 1) which may be made from less abrasion resistant prior art materials. Alternatively, enamel and body portion may be molded from the material of the invention.

In general, the novel compositions of this invention are useful for the formation, construction and repair of dental appliances, artificial teeth, oral prosthesis, and similar articles. In addition, compositions in accordance with the invention are utilized especially as inlay or onlays cemented into or onto teeth, and in the preparation of dental crowns and bridges.

The hardenable dental molding compositions of a preferred interpenetrating network embodiment of the invention include blends of powder and liquid components which are combined in certain proportions and permitted to age or mature to produce a precursor blend that is moldable into prosthetic teeth and other dental devices. The precursor blend is formed by combining polymer and monomer which is then polymerized.

The hardenable dental molding compositions of the invention comprise a blend of powder and liquid components which are combined in certain proportions and are permitted to reach a moldable consistency and are then molded and polymerized by heat and light into a useful desired form. The resulting form may be the finished dental device or it may be machined or otherwise subsequently post-formed to produce the desired shape, as for example a dental inlay formed from a computer assisted design and machining device. The powder may, for example, be comprised of a self-lubricating material, an acrylate or methacrylate polymer or copolymer, a monomer, a crosslinking monomer and/or oligomer, a polymerization catalyst, and optional inorganic filler such as silica, glass, or ceramic.

In a preferred embodiment of the invention product compositions include self-lubricating particles dispersed within an interpenetrating polymer network. Product compositions are formed from precursor blends. Precursor blends are formed by combining particulate self-lubricating material, a crosslinked polymer, a monofunctional monomer and/or a crosslinking monomer and/or oligomer. Optionally precursor blends include uncrosslinked polymer and a polymerization catalyst. Precursor blends are allowed to age or mature and then are molded and polymerized.

The crosslinked polymer is in the form of discrete particles having average diameters ranging form about 0.001 micron to about 500 microns. Preferably, at least 50% by weight of the particles have diameters less than about 150 microns, and more preferably, less than 100 microns. A mixture of two or more different crosslinked polymers may be used. A characteristic of the crosslinked polymer is that it will be insoluble in, but will be swollen by the liquid components used in the preparation of the precursor blend. Uncrosslinked polymer may be characterized as being capable of dissolving in or being dispersed by the liquid components of the blend. The liquid polymerizable monomer blend component of the compositions of the invention have the capacity to dissolve or disperse such uncrosslinked polymer, dissolve or become miscible with the crosslinking agent and swell the particles of crosslinked polymer. A mixture of two or more polymerizable mono and polyfunctional polymerizable monomers which dissolve or become miscible with the crosslinking agent and swell the particles of crosslinked polymer are used as the polymerizable monomer component of the composition of the invention.

Crosslinked powder used in a preferred embodiment of the invention is prepared from polyfunctional and/or monofunctional monomers which are polymerized, e.g. by bulk, solution, suspension or emulsion technics and comminuted to the preferred size ranges if necessary.

Monofunctional Monomers for Preparation of Crosslinked Polymer Powder

Monomers useful in the production of the crosslinked polymers used in the practice of preferred embodiments of the invention include methyl-, ethyl-, isopropyl-, tert-butyloctyl-, dodecyl-, cyclohexyl-, chloromethyl-, tetrachloroethyl-, perfluorooctyl-, hydroxyethyl-, hydroxypropyl-, hydroxybutyl-, 3-hydroxy-phenyl-, 4-hydroxy-phenyl-, aminoethyl-, aminophenyl-, and thiophenyl-, acrylate, methacrylate, ethacrylate, propacrylate, butyl acrylate and chloromethacrylate, as well as the homologous mono-acrylic acid esters of bisphenol-A, dihydroxydiphenyl sulfone, dihydroxydiphenyl ether, dihydroxybiphenyl, dihydroxydiphenyl sulfoxide, and 2,2 bis(4-hydroxy-2,3,5,6-tetrafluorophenyl)propane, as examples only. Other suitable species will be apparent to those skilled in the art, some of which are later recited below.

Polyfunctional Monomers for Preparation Of Crosslinked Polymer Powder

Crosslinking agents which are useful in the production or the crosslinked polymer component of a preferred embodiment of the invention include a wide variety of di- or polyfunctional moieties which are capable of crosslinking monomer species, for example, acrylic and lower alkyl acrylic acid diesters, acrylic and lower alkyl acrylic acid esters formed from alcohols having a second reactive function such as allyl methacrylate, urethane diacrylates and dimethacrylates, polyvinylic compounds, divinyl aromatic compounds, esters of di- or polyfunctional unsaturated acids, e.g., maleic, fumaric, citraconic, mesaconic, itaconic, malonic, or aconitic, etc., acids preferably reacted with either monohydric or poly-hydroxylic saturated and unsaturated alcohols to form esters which are effective polyfunctional crosslinking agents useful in the formulation of the crosslinked polymers of the invention. In general, these alcohols have one or more hydroxylic functionalities and have from 2 to about 30 carbon atoms. Thus, useful alcohols include allyl, methallyl, crotyl, vinyl, butenyl, isobutenyl and similar unsaturated alcohols as well as polyols such as ethylene glycol, propylene glycol, butylene glycol, diethylene glycol, triethylene glycol, tetraethylene glycol, pentaethylene glycol, glycerol, 1,3,3-tri-methylolpropane, pentaerythritol, dihydroxyphenol, and alkylidene bisphenols such as bisphenol-A, 1,1-bis(4-hydroxy-phenyl)-methane, 4,4'dihydroxybiphenyl, 4,4'-dihydroxydiphenyl sulfone, dihydroxydiphenyl ether, dihydroxydiphenyl sulfoxide, resorcinol, hydroquinone, etc. and esters of a mono- or dibasic unsaturated acid with an unsaturated mono-hydroxylic alcohol such as allyl acrylate, allyl methacrylate, vinyl acrylate (methacrylate and $C_1$ to $C_{20}$ homologs), dimethallyl fumarate, N-allyl acrylamide, crotyl acrylate, allyl crotonate, allyl cinnamate, diallyl maleate, etc. di-, tri-, and higher esters of polyhydroxylic alcohols such as ethylene "glycol" diacrylate (dimethacrylate and $C_2$–$C_{40}$ homologs), trimethylolpropane trimethacrylate, the diacrylate and dimethacrylate esters of bisphenol-A, as well as acrylate and alkyl acrylate esters which correspond to the general formula (II):

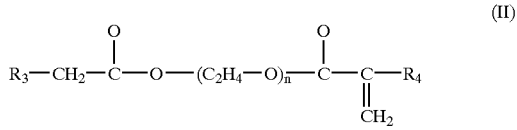

(II)

where R and R, may be the same or different and are hydrogen or alkyl groups containing from 1 to about 6 carbon atoms and n is a whole number from 1 to about 10. Alternatively, the crosslinking agent may conform to the formula (III)

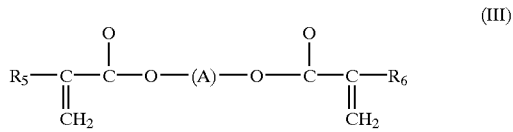

(III)

where $R_5$ and $R_4$ may be the same or different and are hydrogen or alkyl groups containing from 1 to about 6 carbon atoms and A is an aromatic moiety selected from the group consisting of (a) biphenyl, diphenyl alkylidene having from 1 to about 6 carbon atoms in the alkylidene portion thereof, diphenyl sulfone, diphenyl sulfoxide, diphenyl ether, and diphenyl sulfide; (b) the diglycidyl derivatives of group (a); and (c) the diurethane derivatives of either group (a) or group (b). Additional examples include allyl acrylate, divinyl (trivinyl or higher homologs) benzene, substituted divinyl benzenes, and analogous compounds. Compounds such as bis-GMA and the urethane diacrylate formed by reacting hydroxyethyl acrylate, hydroxypropyl acrylate and their methacrylic homologs with 2,4,4-trimethylhexyl-1,6-diisocyanate are especially useful, as are diallyl maleate, ethylene glycol dimethacrylate, trimethylolpropane trimethacrylate and the dimethacrylate ester of bisphenol-A.

Furthermore, mixtures of two or more crosslinking agents are useful in the practice of the invention.

Preparation of Crosslinked Polymer Powder

Crosslinked polymer which may be prepared from the ingredients above or others which are useful in the practice of a preferred interpenetrating network embodiment of the invention are formed from monomers or blends of monomers together with crosslinking agents. The monomers suitable for use in the production of the crosslinked polymers include acrylic and lower alkyl acrylic acid esters, N-vinyl lactams, acrylamides, acrylonitriles, styrenes, alkenes, and urethanes. Preferred monofunctional monomeric species useful in the preparation of the composition of the invention include acrylic and lower alkyl acrylic acid esters which generally conform to the general formula (IV):

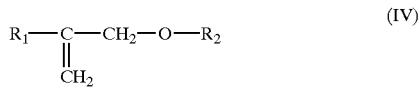

(IV)

wherein $R_1$ is hydrogen or an alkyl group including from 1 to about 6 carbon atoms, and where $R_2$ is either (a) an alkyl or cycloalkyl group including from 1 to about 20, and preferably from 1 to about 6 carbon atoms; (b) phenyl and (c) alkyl substituted phenyl in which the alkyl groups include form 1 to about 6 carbon atoms. Various substituents may be present on either or both of the groups $R_1$ and $R_2$. Thus, hydroxyl, carboxyl, amino, thliol and halogen e.g., fluorine, chlorine, etc.) functionalities may be present, with the latter being preferred. Fluorine is an especially suitable and useful substituent.

The crosslinked polymer powders are produced by polymerizing a mixture of the monomer or monomers and crosslinking agent or agents described above. The amount of crosslinking agent employed in the production of the crosslinked polymers used in the practice of the invention is a critical factor. It has been found that the capacity of particles of polymers so produced to swell with or to imbibe the liquid components forming the precursor blend of the invention, is directly related to the amount of crosslinking agent used in the production of such crosslinked polymers.

The physiochemical properties of the crosslinked polymer fillers useful in the preferred interpenetrating network embodiment of the invention determine the relative proportions of monomer and crosslinking agent used to formulate said suitable crosslinked polymers. Such crosslinked polymers must be sufficiently well crosslinked as to maintain substantially their structural identity when exposed to the liquid components of the precursor blend of the invention. At the same time, they must not be so thoroughly crosslinked as to be incapable of swelling with or imbibing such liquid components. Thus, it is convenient to describe the proportion of crosslinking agent by what it does rather than by what it is. In view of the fact that the crosslinked polymers are utilized in finely particulate form, as will be more fully explained, it is convenient to define the minimum amount of crosslinking agent used therein as being that amount which is sufficient to cause the particulate crosslinked polymer not to lose its particulate discreteness upon exposure to the liquid components of the invention. Similarly, the maximum amount of crosslinking agent used therein is that amount beyond which the resulting crosslinked polymer particles are unable to swell with or further imbibe a significant portion of liquid components upon exposure thereto. In this regard, a quantity of crosslinked polymer particles would be said to swell with or imbibe a significant portion of liquid components if it swelled with or has imbibed at least 10% of its own weight of such liquid. Preferably, an amount of crosslinking agent is used to provide a crosslinked polymer having the capacity to imbibe from about 10 to about 500 percent of its own weight of liquid components.

It will be clear to those skilled in the art that the minimum and maximum values for the proportions of crosslinking agents suitable for inclusion in the crosslinked polymers of this invention will vary depending upon the chemical identity of the component monomers and crosslinking agents. In general, however, the crosslinking agents may comprise from as low as about 0.01% to as high as about 100 and preferably from about 0.2% to about 40 by weight of the resulting crosslinked polymer.

The production of the crosslinked polymer useful in the preferred interpenetrating network embodiment of the invention from monomers and crosslinking agents may be performed by any of the many processes known to those skilled in the art. Thus, the polymers may be formed by heating a mixture of the components to a temperature sufficient to cause polymerization, either with or without the addition of initiators. For this purpose, peroxy type initiators such as benzoyl peroxide, dicumyl peroxide and other materials familiar to those skilled in the art may be employed and the use of activators may be advantageous in some formulations. Alternatively, the crosslinked polymers of the invention may be formed from the constituents by photochemical or radiant initiation utilizing light or high energy radiation.

The polymerization of the crosslinked polymers may be accomplished in a wide variety of ways all of which are known to those skilled in the art. Thus, they may be formed by suspension polymerization (as taught by Grim in U.S. Pat. No. 2,673,194), emulsion polymerization, block polymerization. The crosslinked particles preferably have an average particle size should be from about 0.001 micron to about 500 microns. It is preferred that at least 50% by weight of the particles have diameters below 150 microns and more preferably below 100 microns.

Uncrosslinked Polymer Powders

In addition to the crosslinked polymers described above, the polymer component of the precursor blend of a preferred embodiment of the invention may comprise an uncrosslinked polymer. Such uncrosslinked polymer include those formed from any of the monofunctional monomer species which have been disclosed above as being useful for the preparation of the crosslinked polymers used in the practice of the invention. Thus, monomer species conforming to the formula above, the acrylic and $C_1$ to $C_6$ lower alkyl acrylic esters of aliphatic alcohols having from 1 to about 20 carbon atoms, or mixtures thereof, are suitable as is vinylidene fluoride. Polymeric methyl methacrylate and copolymers thereof are preferred. The uncrosslinked polymers may be formed from the monomers through any of the polymerization procedures known to those skilled in the art. Thus, thermal or photochemical polymerization, either with or without initiators, sensitizers, activators or chain transfer agents may be employed. Similarly, either bulk, suspension or emulsion polymerization may be utilized. Preferably, the uncrosslinked polymers should be characterized as having average molecular weight of from about 100,000 to about 2,000,000 g/mole, and especially of from about 500,000 to about 900,000 g/mole. While the polymers are used in particulate form, they differ from the crosslinked polymer filler in that, unlike the crosslinked polymers, the uncrosslinked polymers do not have a critical particle size distribution. Thus, polymer particles or beads of any conveniently small size such as about 50 microns, may be utilized. Smaller sizes are preferred since they imbibe monomers and will dissolve therein more readily, but larger sizes may be used as well.

Polymerizable Liquid Monomer Blend

Polymerizable monomers suitable for use in the formulation of the precursor blend of a preferred embodiment of the invention may comprise any of a wide variety of monomers including those previously described examples provided in the preparation of crosslinked and uncrosslinked polymer powder. Thus, acrylic and lower alkyl acrylic acid esters, N-vinyl lactams, acrylimides, acrylamides, acrylonitriles, styrenes, alkenes, urethane acrylate or methacrylate and other monomeric species may be employed in the practice of the invention.

Especially preferred examples of polymerizable monomers useful in the practice a preferred embodiment of the invention include methyl-, ethyl-, isopropyl-, t-butyl-, octyl-, dodecyl-, cyclohexyl-, chloromethyl-, tetrachloroethyl-, perfluorooctyl-, hydroxyphenyl-, hydroxypropyl-, hydroxybutyl-, 3-hydroxyphenyl-, 4-hydroxyphenyl-, aminoethyl-, aminophenyl-, and thiophenyl-, acrylate, methacrylate, ethacrylate, propacrylate, butacrylate and chloromethacrylate, as well as the homologous mono-acrylic acid esters of bisphenol-A, dihydroxydiphenyl sulfone, dihydroxydiphenyl ether, dihydroxybiphenyl, dihydroxydiphenyl sulfoxide, and 2,2-bis(4-hydroxy-2,3,5,6-tetrafluorophenyl)propane. Other suitable species will be apparent to those skilled in the art who will further recognize that mixtures of two or more different polymerizable monomers may be used. Polyfunctional Monomers And Oligomer Components Of Polymerizable Liquid Blend Preferably, the crosslinking agents for the polymerizable monomers comprise esters of unsaturated acids, e.g., acrylic, methacrylic, ethacrylic, propacrylic, butacrylic, etc. maleic, fumaric, citraconic, mesaconic, itaconic, malonic, or aconitic, etc., acids. Other unsaturated acids will be readily apparent to those skilled in the art. These acids are preferably reacted with either unsaturated or polyhydroxylic alcohols to form esters which are effective polyfunctional crosslinking agents for the monomeric species useful in the practice of the invention. Thus, useful alcohols include allyl, methallyl, crotyl, vinyl, butenyl, isobutenyl and similar unsaturated alcohols as well as polyols such as ethylene glycol, propylene glycol, butylene glycol, diethylene glycol, triethylene glycol, tetraethylene glycol, pentaethylene glycol, glycerol, trimethylolpropane, pentaerythritol, dihydroxyphenol, alkylidene bisphenols such as bisphenol-A; 1,1-bis (4-hydroxyphenyl) methane; 4,4'-dihydroxybiphenyl; 4,4'-dihydroxydiphenyl sulfone; dihydroxydiphenyl ether; dihydroxydiphenyl sulfoxide; resorcinol; hydroquinone; etc.

Preferred crosslinking agents used in the practice of the invention include those previously described examples provided for in preparation of crosslinked and uncrosslinked polymer powders as well as, the esters of a monomeric dibasic unsaturated acid with an unsaturated monohydroxylic alcohol such as allyl acrylate, allyl methacrylate, vinyl acrylate (methacrylate and homologs), dimethallyl fumarate, N-allyl acrylamide, crotyl acrylate, allyl crotonate, allyl cinnamate, diallyl maleate, etc. Other preferred species are the di-, tri-, and higher esters of polyhydroxylic alcohols such as ethylene "glycol" diacrylate (dimethacrylate and $C_f$–$C_6$ homologs), trimethlolpropane trimethacrylate, and the dimethacrylate ester of bis-phenol-A as well as other acrylate and allyl acrylate esters. In addition, the crosslinking agent for the polymerizable monomers may be a glycidyl acrylate r allyl acrylate, divinyl (trivinyl or higher homologs) benzene, substituted divinyl benzenes, or analogous compounds. Furthermore, mixtures of crosslinking agents are useful in the practice of the invention.

Compounds such as those described herein above as crosslinking agents and bis-G A and the urethane dimethacrylate formed from the reaction of hydroxyethyl acrylate, hydroxypropyl acrylate and their methacrylate homologs with 2,4,4-trimethylhexyl-1,6-diisocyanate (hereinafter referred to as "urethane dimethacrylate" or "diacrylate") are especially useful, as are ethylene glycol dimethacrylate, trimethylolpropane trimethacrylate and the dimethacrylate ester of bisphenol-A. The corresponding acrylates are similarly useful as is diallyl maleate.

Additional Ingredients

In addition to the components described above, (i.e., crosslinked polymer, uncrosslinked polymer, polymerizable monomer) the precursor blend may contain additional, optional, ingredients, such as, initiators, activators, pigments, fillers, radiopaquing agents, adhesion modifiers, free radical or photochemical initiators. In this regard, peroxy type initiators such as dicumyl or benzoyl peroxide are useful. Similarly, pigments and fillers may be added to modify the appearance, density, and physical characteristics of the resultant dental appliances. Inorganic materials, especially silica and titania, silicates and aluminates, glasses and ceramics are useful fillers and pigments, and a wide variety of other useful pigments and fillers will be apparent to those skilled in the art. The fillers and radiopaquing agents may constitute a major part by weight of the compositions of the invention. According to a preferred embodiment, the precursor blend of this invention may comprise admixtures of organic resin components and particulate, inorganic filler in weight ratios of from about 1:2 to about 2:1 or more depending on the specific gravity of inorganic ingredients included.

Precursor Blends

The precursor blends in accordance with a preferred embodiment of the invention are formulated by a mixing together of the constituent species in proper proportion, followed by aging or maturing. Several techniques are available for this and others will be apparent to those skilled in the art. Thus, it is possible to combine crosslinked polymer filler, self-lubricating particles, uncrosslinked polymer and polymerizable liquid bland in proper proportions including therewith, for example, a peroxide initiator and a pigment. This combination is then thoroughly mixed and aged to result in a precursor blend which has a uniform appearance. This blend may have the consistency of dough or may be more or less mobile depending upon the desired use thereof. Particulate inorganic fillers or other modificants may be preferably added at this stage in the formulation of the compositions if desired. The compositions thus formed may be alternatively molded, extruded, brushed, formed, worked or otherwise shaped in any conventional manner and caused to polymerize or cure to result in hard dental appliances having superior properties. The application of heat or radiant energy is usually required for this polymerization or curing.

It is especially useful to mold the compositions of this invention into artificial teeth for inclusion in prosthetic devices. It is to be understood, however, that the precursor blends are suitable for a very wide range of dental uses, including fillings, teeth, bridges, crowns, veneers, facings, denture base and denture reline materials, and orthodontic splint materials, and the like. The materials of the invention may also be utilized for prosthetic replacement or repair of various hard body structures such as bone and may be utilized for reconstructive purposes during surgery.

The nature of the chemical and physical relationships among the components of the precursor blends of the invention is important to the practice of the invention. Among these relationships is the necessity that the crosslinked polymer particles be capable of swelling by imbibing the liquid components. Of similar importance is the requirement that the uncrosslinked polymers, when included, be capable of dissolving in the liquid components. The precursor blend formed by any of the useful techniques described above is aged for a period of time sufficient to insure that in one embodiment the crosslinked polymer has become substantially fully swollen with, interpenetrated by or has substantially imbibed the liquid crosslinking blend and that the uncrosslinked polymer, if used, has at least partially been dissolved therein. Thus, as used herein, "aged" or "aging" refer to the maintenance of the components of the precursor blend in association with one another in the blend for a period of time sufficient to substantially fully swell the crosslinked polymer particles with the mixture of polymerizable monomer and crosslinking agent dissolved therein. Frequently, aging is manifested by a change in the consistency of the mixture as equilibrium is approached. The time necessary to approach such equilibrium will vary depending upon the blending techniques, the relative proportions of materials, the particle sizes and molecular weights of the polymers and the temperature extent in the mixtures. In general, aging time of from one to seven days has been found to be adequate to approach the desired equilibrium. It is to be understood that it lies well within the abilities of those skilled in the art to ascertain the optimum aging time for a formulation in view of the foregoing considerations. In accordance with this preferred technique, powder components including self-lubricating abrasion resistant particles are blended with a polymerizable liquid blend. The precursor blend is then aged for a period of time sufficient to permit the crosslinked polymer particles to be substantially fully swollen with, or interpenetrated by polymerizable blend. Precursor blends thus formed may be alternatively molded, brushed, extruded, formed, worked or otherwise shaped to form useful dental devices and articles. Other techniques are presented in the examples which follow, and still others will be apparent to those skilled in the art.

Upon polymerization of the precursor blends in one embodiment a three dimensional structure is believed to be formed which may be denominated as an interpenetrating polymeric network. The interpenetrating network structure which is believed to form is a major contributing factor to the serendipitous combination of superior chemical and physiochemical properties which is exhibited by the articles constructed according to the practice of the invention. Interpenetrating polymeric networks are related to, but distinct from, traditional graft polymers.

Interpenetrating Network Moldings

In accordance with a preferred embodiment of the invention a self-lubricating interpenetrating network may be viewed as being composed of ultra high molecular weight polyethylene dispersed within two or more crosslinked, and hence three dimensionally arrayed, polymeric networks which do not necessarily have any covalent bonds in common. While the two net-works may, indeed, be independent in the sense that they need possess no covalent linkages between them; they are physically trapped one "within" the other and cannot disassociate by any physical manipulation without the rupture of covalent bonds. Particulate crosslinked polymer is allowed to swell with or imbibe monomer mixed with crosslinking agent, and when the imbibed mixture of monomer and crosslinking agent is subsequently caused to polymerize, an interpenetrating polymeric network may be seen to be formed within the confines of the particulate crosslinked polymer. It is believed that the aging process employed in the preparation of the precursor blends of the invention is required to accomplish substantially full swelling with interpenetration by or substantially complete inbibition of crosslinking agent by the crosslinked polymer particles, and to approach an equilibrium thereof.

The American Dental Association specification number 15 specifies, "the strength of the bond between tooth and resin is tested in tension. The minimum bond strength is 30.9 $MN/M^2$(4,480 psi; 315 $Kg/cm^2$), which is sufficient to prevent separation of the teeth from the resin denture base in use." This pertains to "acrylic denture base resin polymerized by the heat processing technique." The compositions of this invention meet or exceed this specification.

A unique, heterogeneous microstructure is exhibited by one embodiment, the preferred interpenetrating network embodiment of the invention. One exemplary method for observing this microstructure is as follows:

1. The tooth, or molded article, is sectioned and one section patted in epoxy against a flat surface.
2. The sectioned surface of the potted specimen is polished to a smooth surface using nos. 320, 400 and 600 grit silicon carbide papers wet continuously with water.
3. A final polish is obtained using an aqueous slurry of 0.3 micron $Al_2O_3$ on a chamais.

4. The polished surface of the section is exposed for four minutes to the vapors of boiling concentrated nitric acid; the microstructure is oxidatively exposed by this etching procedure and is best captured by photomicrography at 260× magnification.

The microstructure thus observed is heterogeneous and comprises what may best be described as particles suspended in a matrix. The particles are believed to be identifiable with the particulate crosslinked polymers of the precursor blend which have been swollen by and interpenetrated with the monomer and crosslinking agent. By comparison with conventional composite compositions containing only rigid inorganic fillers, the articles formed according to the present invention exhibit a microstructure in which the structure is much more closely packed. It is to be understood that this methodology, while of wide application in the examination of the microstructure of the novel compositions of the invention, is not exclusive. Other techniques involving greater or lesser magnification and other means of visualization are also useful in disclosing the structure. Distributed throughout this structure is particulate self-lubricating particles.

Preferably teeth formed in accordance with a preferred embodiment of the invention are from 0.1 to 80 percent by weight self-lubricating material having a kinetic coefficient of friction less than 0.25 when measured using ASTM D 1894-78 and 5 psi.

Preferably, the self-lubricating materials for use in accordance with the invention have an average largest dimension (or diameter) from 0.5 to 80 microns. More preferably, such particles have an average largest dimension (or diameter) less than 70 microns. Most preferably, the self-lubricating particles for use in accordance with the invention have an average largest dimension (or diameter) from 1 to 80 microns. Most preferably, the self-lubricating particles for use in accordance with the invention have an average largest dimension (or diameter) from 2 to 20 microns. A preferred embodiment of the invention provides a tooth including polyethylene having a molecular weight of at least 500,000 and preferably a molecular weight of at least 1,000,000, and a particle size less than 80 microns. In a preferred embodiment of the invention a dental prosthesis is provided including polyethylene, particles having a particle size less than 80 microns and a molecular weight of at least 3,000,000 functionalized by gas plasma treatment so as to be bondable to the matrix polymer.

The following examples describe certain representative embodiments of this invention and will serve further to illustrate the nature thereof. It is to be understood that the examples are merely illustrative, and do not in any way limit the scope of the invention as defined by the claims. All percentages are by weight.

COMPARATIVE EXAMPLE 1
Prior Art IPN Tooth

A precursor blend is prepared from the following composition:

| | |
|---|---|
| 37.81% | methyl methacrylate |
| 0.23% | benzoyl peroxide |
| 7.96% | 2,2-bis(4-methacryloxyphenyl)propane |
| 35.62% | poly(methyl methacrylate-co-ethylene dimethacrylate) (99.2:0.8) |
| 17.80% | poly(methyl methacrylate) |
| 0.58% | pigment |
| 100.00% | |

The crosslinked polymer is in the form of particles, 46% by weight of which were below 74 microns in size, the balance being below about 500 microns in size. The poly(methyl methacrylate) have an average molecular weight of 800,000 g/mole.

The benzoyl peroxide and 2,2-bis(4-methacryloxyphenyl)propane are dissolved in the methyl methacrylate at ambient temperature to form a monomer solution. The polymers and pigment are charged to a planetary dough mixer containing the monomer solution and the charge is stirred until visibly homogeneous. Prosthetic teeth are molded from the resultant precursor blend mixture after it is aged at ambient temperature for seven days. The resulting teeth grind with a dusty, fine debris, bond to denture base and are impact and wear resistant.

EXAMPLE 2
Interpenetrating Network Teeth

The method described in Example 1 is used to prepare a precursor blend from which prosthetic teeth are molded having the following composition:

| | |
|---|---|
| 26.83% | methyl methacrylate |
| 4.00% | ultrahigh molecular weight polyethylene (Hoechst, AG) treated with oxygen and fluorine (50 micron largest particle dimension) |
| .17% | benzoyl peroxide |
| 2.11% | 2,2,2-trifluoroethyl acrylate |
| 2.37% | ethylene glycol dimethacrylate |
| 1.52% | reaction product of hydroxypropyl methacrylate with 2,2,4-trimethylhexyl-1,6-disocyanate(2:1) (urethane dimethacrylate) (UDMA) |
| 41.30% | poly(methyl methacrylate-co-ethylene dimethacrylate) (98.8:1.2) |
| 20.65% | poly(methyl methacrylate) |
| 1.05% | pigment |
| 100.00% | |

A suitable gel-like consistency for molding prosthetic teeth is obtained after aging at ambient temperature for 24 hours. The high molecular weight self-lubricating polyethylene had a molecular weight of approximately 4,000,000 and was obtained from Hoechst-Celanese Inc. Particle surfaces were oxyfluorinated in the presence of a fluorine and oxygen at high temperature to be capable of bonding to the matrix material within which it was dispersed.

EXAMPLE 3
Interpenetrating Network Teeth

The following composition yielded a precursor blend which is molded into prosthetic teeth after processing according to the technique of Example 1.

| | |
|---|---|
| 45.83% | methyl methacrylate |
| 4.00% | ultrahigh molecular weight polyethylene treated with oxygen and fluorine (50 micron largest particle dimension |
| 0.17% | benzoyl peroxide |
| 11.50% | bis-GMA |
| 24.80% | poly(methyl methacrylate-co-ethylene dimethacrylate) (70:30) |
| 11.90% | poly(methyl methacrylate) |
| 1.80% | pigment |
| 100.00% | |

EXAMPLE 4
Interpenetrating Network Teeth

A two-step "preswell" mixing method is used to prepare a precursor blend from which prosthetic teeth are molded. The blend has the following composition:

| Step 1 | |
|---|---|
| 40.40% | methyl methacrylate |
| 4.00% | ultrahigh molecular weight polyethylene treated with oxygen and fluorine (50 micron largest particle dimension) |
| 0.25% | benzoyl peroxide |
| 6.00% | reaction product of hydroxypropyl methacrylate with 2,2,4-trimethylhexyl-1,6-disocyanate (2:1) (urethane dimethacrylate) (UDMA) |
| 1.50% | 2,2-bis(4-methacryloxyphenyl)propane |
| 47.85% | poly(methyl methacrylate-co-ethylene dimethacrylate) (90:10) |
| 100.00% | |

The crosslinked polymer is in the form of particles, 50% by weight of which are below 100 microns in size, the balance being below about 500 microns in size.

| Step 2 | |
|---|---|
| 28.14% | poly(methyl methacrylate) |
| 60.43% | methyl methacrylate |
| 0.36% | benzoyl peroxide |
| 10.20% | 2,2-bis(4-methacryloxyphenyl)propane |
| 0.87% | pigment |
| 100.00% | |

The poly(methyl methacrylate) has an average molecular weight of 850,000 g/mole.

The weight ratio of Step 1 to Step 2 material in this example is 1.14 to 1.00. Step 1 is achieved by preparing a solution of the monomers, crosslinkers and initiator and adding the crosslinked copolymer. This mixture is stirred for about two minutes to wet the polymer, capped against monomer loss, and held for one week at about 10° C. temperature. The crosslinked copolymer completely absorbed the monomer solution during the one week "preswell" period. Although the copolymer is swollen by this process, the integrity of the individual copolymer particles is maintained. This "preswell" mixture is not gel-like, but has the consistency of a rubbery, spongy mass which is easily crumbled.

Step 2 is achieved by charging "preswell", obtained in Step 1, to a planetary dough mixer and mixing sufficiently so as to break the "preswell" mass of own to a fine consistency. The poly(methyl methacrylate) and pigment are added to the mixer and mixing is continued until a homogeneous dispersion is obtained. The solution of monomer and initiator, cited in the Step 2 composition, is charged to the mixer; mixing continued until a homogeneous, gel consistency is obtained. The gel-like mix is transferred to a holding container and aged at about 10° C. temperature until a suitable consistency for molding prosthetic teeth is obtained, approximately three days.

EXAMPLE 5
One-Component Filled Radiation Curable Material

The following gel composition, containing an inorganic filler and prepared by the method described in Example 1, is polymerized by visible light radiation using a Caulk MAX photo-cure lamp (registered trademark of Dentsply International):

| | |
|---|---|
| 21.21% | methyl methacrylate |
| 3.00% | ultrahigh molecular weight polyethylene treated with oxygen and fluorine (50 micron largest particle dimension) |
| 2.96% | butyl methacrylate |
| 0.27% | camphoroquinone |
| 0.43% | dimethylamino benzoic acid ethyl ester |
| 2.08% | 2,2-bis(4-methacryloxyethoxyphenyl)-propane |
| 1.13% | tetraethylene "glycol" dimethacrylate |
| 1.13% | neopentyl "glycol" dimethacrylate |
| 19.45% | poly(methyl methacrylate-co-2,2-bis-(4-methacryloxyphenyl)propane) (99.8:0.2) |
| 12.23% | poly(methyl methacrylate) |
| 35.66% | silane treated, fine (12 micron) particle quartz |
| 0.45% | pigment |
| 100.00% | |

EXAMPLE 6
Dental Veneers

A two step preswell process is used to mix a one part dental veneer material. A blend is prepared from the following:

| Step 1 | |
|---|---|
| 2.99% | methyl methacrylate |
| 3.00% | ultrahigh molecular weight polyethylene treated with oxygen and fluorine (50 micron largest particle dimension) |
| 0.51% | benzoyl peroxide |
| 45.26% | reaction product of hydroxypropyl methacrylate with 2,2,4-trimethylhexyl-1,6-disocyanate (2:1) (urethane dimethacrylate) (UDMA) |
| 48.24% | poly(methyl methacrylate-co-ethylene dimethacrylate) (99.8:0.2) |
| 100.00% | |

The benzoyl peroxide is dissolved in the methyl methacrylate and blended with the urethane dimethacrylate. This solution is then mixed with the poly(methyl methacrylate-co-ethylene dimethacrylate) (99.8:0.2) and UHMWPE. The mixture is stored in the dark in a sealed jar to become the "pre-swell" blend. The crosslinked polymer i.e. poly(methyl methacrylate-co-ethylenedimethacrylate) (99.8:0.2) is in the form of fine particles at least 50% by weight are below 100 microns in size, and the balance below 500 microns in size. After one month storage the fully swollen crosslinked polymer "preswell" blend is admixed as follows:

| Step 2 | |
|---|---|
| 48.84% | "preswell" blend from Step 1 |
| 51.03% | silane treated microfine silica |
| 0.13% | acrylic acid |
| 100.00% | |

These components are mixed on a three roll mill with minor amounts of pigments as required until a uniformly shaded paste is obtained.

A veneer is prepared on an opaqued crown by the well known build up method. A dentin shade veneer paste is built up on the crown by hand and instrument modelling. Next, an incisor shade veneer paste is built on top of the dentin. The veneer is polymerized by immersion in a 90° C. water bath under three bars air pressure. Veneers are also polymerized by immersion in glycerin in a similar manner. The finished veneer has a high gloss and good aesthetic appearance. The veneer has three times the wear resistance of conventional acrylic veneers by a prophy abrasion test. The veneer can be readily shaped by grinding, yielding a dusty debris, and then is readily polished to a smooth, high gloss finish. The veneer is resistant to chemicals and stains, has good impact strength and is repairable. The veneer paste is stable at ambient conditions. The veneer paste is stable for nine months at ambient and seventy days at 50° C.

EXAMPLE 7
Dental Veneer

A two step preswell process is used to mix a one part dental veneer from the following composition:

Step 1

"Preswell" blend from Example 6 aged 22 days at ambient.

| Step 2 | |
|---|---|
| 57.29% | "preswell" blend from Step 1 |
| 41.67% | silane treated microfine silica |
| 1.04% | acrylic acid |
| 100.00% | |

The components are mixed on a three roll mill until visually uniform. The putty-like material is formed into a dental veneer and polymerized by immersion in 90° C. glycerin at three bars pressure for ten minutes to yield shapable, durable and aesthetically superior appliances.

EXAMPLE 8

| TOOTH MATERIAL | |
|---|---|
| 60.00% | polymethymethacrylate 800,000 average molecular weight |
| 31.35% | methylmethacrylate |
| 3.48% | ethylene glycol dimethacrylate |
| 0.17% | benzoyl peroxide |
| 5.0% | ultra high molecular weight polyethylene, surface treated |
| 100.00% | |

Ultra high molecular weight polyethylene (PRIMAX) and polymethyl methacrylate 800,000 average molecular weight are dispersed in one another in a high shear mixer. The powder and liquid components are then combined in a planetary mixer and stored for one week to achieve a suitable consistency for molding. Teeth are molded using heat and pressure in closed mold to form artificial teeth according to the invention.

EXAMPLE 9
Tooth Material

A precursor blend is prepared from the following composition:

| | |
|---|---|
| 37.3% | silica, as in EXAMPLE 8, but not silanated |
| 17.4% | methyl methacrylate |
| 0.5% | benzoyl peroxide |
| 17.4% | ethylene glycol dimethacrylate |
| 14.9% | poly(methyl methacrylate) |
| 25.% | ultrahigh molecular weight polyethylene as in EXAMPLE 8. |
| 100.00% | |

Ingredients are mechanically mixed in a closed container until a viscous paste is obtained. This paste is introduced into a tooth mold and polymerized for 4 minutes at 110° C. The artificial tooth thus obtained shows clear opalescence, i.e. it appears yellowish in transmitted light and of a blue-white transparency in incident light. The ball indentation hardness is 2800 kg/cm$^2$ as compared with 1400 kg/cm$^2$ in the case of comparison teeth compared on basis of the customary methacrylate.

EXAMPLE 10
Self-Lubricating Abrasion Resistant IPN Tooth

A precursor blend is prepared from the following composition:

| | |
|---|---|
| 18.16% | high molecular weight poly(methyl methacrylate) polymer |
| 36.26% | poly(methyl methacrylate-co-ethylene dimethacrylate) (99.2:0.8) |
| 7.45% | 2,2-bis(4-methacryloxyphenyl)propane |
| 6.82% | reaction product of hydroxypropyl methacrylate with 2,2,4-trimethylhexyl-1,6-disccyanate (2:1) (urethane dimethcrylate) (UDMA) |
| 28.52% | methylmethacrylate |
| 0.21% | benzoyl peroxide |
| 2.28% | ultra high molecular weight polyethylene |
| 0.33% | pigments |
| 100.00% | |

The UHMWPE and crosslinked polymer is in the form of particles, 46% by weight of which were below 74 microns in size, the balance being below about 500 microns in size. The poly-(methyl methacrylate) has an average molecular weight of 800,000 g/mole.

The tooth is evaluated for wear resistance in a computer programmed chewing device (Journal of Prosthetic Dentistry, Volume 54, Number 2, August 1985, pages 273–280). It demonstrates a volume loss from wear against a natural tooth of 0.021 mm$^3$, compared to 0.032 mm$^3$ loss for commercial tooth, BIOFORM (Dentsply) prepared in general according to U.S. Pat. No. 4,698,373.

TABLE 1

Comparison of tooth wear:

| Example | Tooth wear g/10,000 cycles | Percent Reduction in wear |
|---|---|---|
| 1 (Prior Art tooth) | 0.0327 | 0 |
| 10 | 0.0247 | 25 |

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A method of making an interpenetrating polymer network artificial dental tooth having a reduced coefficient of friction and adapted for use in combination with denture base formed into a denture, comprising:

forming a tooth body consisting essentially of an interpenetrating polymer network having a polymer matrix, said interpenetrating polymer network being formed by polymerization of monomers of a polymer matrix forming composition, said polymer matrix forming composition comprising a blend of particulate material and liquid polymerizable monomers, said liquid polymerizable monomers comprising monofunctional polymerizable monomer and di or polyfuncational crosslinking agent reactive with said polymerizable monomer, said particulate material comprising from about 10% to about 70% by weight of said tooth body, said particulate material comprising self lubricating polymer particles and crosslinked polymer particles having average diameter up to about 500 microns, said crosslinked polymer particles being sufficiently crosslinked as to maintain substantially their structural identity when exposed to said monomers, said crosslinked polymer particles being substantially swollen by imbibing at least 10% by weight of said crosslinked polymer particles of said monomers, said self-lubricating particles comprising a polymer of the general formula:

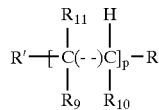

wherein p is an integer from 100 to 1,000,000,
(- -) is a single or a double bond;
when (- -) is a double bond R, R' and $R_{11}$ independently are hydrogen, or a lower alkyl of from 1 to 6 carbons, and $R_9$ and $R_{10}$ are not present; when (- -) is a single bond R, R', $R_9$, $R_{10}$, and $R_{11}$ independently are hydrogen, fluorine or a lower alkyl of from 1 to 6 carbons, said self-lubricating particles being effectively bonded to and distributed in said polymeric matrix, said interpenetrating polymer network artificial tooth comprising at least 0.1 percent by weight of said self-lubricating particles and said interpenetrating polymer network artificial tooth effectively having a reduced coefficient of friction compared to said interpenetrating polymer network artificial tooth from which said self-lubricating particles are omitted, said tooth being adapted to bond with a bond strength between said tooth and said denture base of at least 4,480 psi.

2. The method of claim 1 wherein said self-lubricating particles have a particle size less than 500 microns.

3. The method of claim 1 wherein about 46 percent by weight of said self-lubricating particles have a particle size less than 74 microns.

4. An improved method of making an interpenetrating polymer network artificial dental tooth adapted for use in combination with denture base formed into a denture, comprising:

forming a tooth having a tooth body consisting essentially of an interpenetrating polymer network having a polymer matrix, said interpenetrating polymer network being formed by polymerization of monomers of a polymer matrix forming composition, said polymer matrix forming composition comprising a blend of particulate material and liquid polymerizable monomers, said liquid polymerizable monomers comprising monofunctional polymerizable monomer and di or polyfuncational crosslinking agent reactive with said polymerizable monomer, said particulate material comprising from about 10% to about 70% by weight of said tooth body, said particulate material comprising crosslinked polymer particles having average diameter up to about 500 microns, said crosslinked polymer particles being sufficiently crosslinked as to maintain substantially their structural identity when exposed to said monomers, said crosslinked polymer particles being substantially swollen by imbibing at least 10% by weight of said crosslinked polymer particles of said monomers, the improvement wherein said particulate material comprises self-lubricating particles effectively bonded to and distributed in said polymeric matrix, said self-lubricating particles comprising a polymer of the general formula:

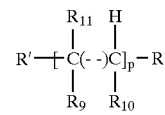

wherein p is an integer from 100 to 1,000,000,
(- -) is a single or a double bond;
when (- -) is a double bond R, R' and $R_{11}$ independently are hydrogen, or a lower alkyl of from 1 to 6 carbons, and $R_9$ and $R_{10}$ are not present; when (- -) is a single bond R, R', $R_9$, $R_{10}$, and $R_{11}$ independently are hydrogen, fluorine or a lower allyl of from 1 to 6 carbons said tooth comprising at least 0.1 percent by weight of said self-lubricating particles, said tooth being adapted to bond with a bond strength between said tooth and said denture base of at least 4,480 psi.

5. The method of claim 4 wherein said self-lubricating particles have a particle size less than 500 microns.

6. The method of claim 4 wherein about 46 percent by weight of said self-lubricating particles have a particle size less than 74 microns.

7. An improved method of making an interpenetrating polymer network artificial dental tooth adapted for use in combination with denture base formed into a denture, comprising:

forming a tooth having a tooth body consisting essentially of an interpenetrating polymer network having a polymer matrix, said interpenetrating polymer network being formed by polymerization of monomers of a polymer matrix forming composition, said polymer matrix forming composition comprising a blend of particulate material and liquid polymerizable monomers, said liquid polymerizable monomers comprising monofunctional polymerizable monomer and di or polyfuncational crosslinking agent reactive with said polymerizable monomer, said particulate material comprising from about 10% to about 70% by weight of said tooth body, said particulate material comprising crosslinked polymer particles having average diameter up to about 500 microns, said crosslinked polymer particles being sufficiently crosslinked as to maintain substantially their structural identity when exposed to said monomers, said crosslinked polymer particles being substantially swollen by imbibing at least 10% by weight of said crosslinked polymer particles of said monomers, said product being made by the process comprising adding self-lubricating particles to said particulate material, said self-lubricating particles being effectively bonded to and distributed in said polymeric matrix, said self-lubricating particles comprising a polymer of the general formula:

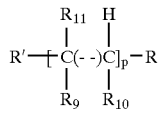

wherein p is an integer from 100 to 1,000,000,
(- -) is a single or a double bond;
when (- -) is a double bond R, R' and $R_{11}$ independently are hydrogen, or a lower alkyl of from 1 to 6 carbons, and $R_9$ and $R_{10}$ are not present; when (- -) is a single bond R, $R_1$, $R_9$, $R_{10}$, and $R_{11}$ independently are hydrogen, fluorine or a lower alkyl of from 1 to 6 carbons, said tooth comprising an effective amount of said self-lubricating particles, said tooth being adapted to bond with a bond strength between said tooth and said denture base of at least 4,480 psi.

8. The method of claim 7 wherein said self-lubricating particles have a particle size less than 500 microns.

9. The method of claim 7 wherein about 46 percent by weight of said self-lubricating particles have a particle size less than 74 microns.

10. A method of making an interpenetrating polymer network artificial dental tooth having a reduced coefficient of friction and adapted for use in combination with denture base formed into a denture, comprising:

forming a tooth body comprising an interpenetrating polymer network having a polymer matrix, said interpenetrating polymer network being formed by polymerization of monomers of a polymer matrix forming composition, said polymer matrix forming composition comprising a blend of particulate material and liquid polymerizable monomers, said particulate material comprising self lubricating polymer particles having a particle size less than 500 microns and crosslinked polymer particles having average diameter up to about 500 microns, said self-lubricating particles being effectively bonded to and distributed in said polymeric matrix, said self-lubricating particles comprising a polymer of the general formula:

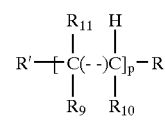

wherein p is an integer from 100 to 1,000,000,
(- -) is a single or double bond;
when (- -) is a double bond R, R' and $R_{11}$ independently are hydrogen, or a lower alkyl of from 1 to 6 carbons, and $R_9$ and $R_{10}$ are not present; when (- -) is a single bond R, R', $R_9$, $R_{10}$, and $R_{11}$ independently are hydrogen, fluorine or lower alkyl of from 1 to 6 carbons, said interpenetrating polymer network artificial tooth comprising at least 0.1 percent by weight of said self-lubricating particles and said interpenetrating polymer network artificial tooth effectively having a reduced coefficient of friction compared to said interpenetrating polymer network artificial tooth from which said self-lubricating particles are omitted, said tooth being adapted to bond with a bond strength between said tooth and said denture base of at least 4,480 psi.

* * * * *